US009084895B2

(12) United States Patent
Greenberg et al.

(10) Patent No.: US 9,084,895 B2
(45) Date of Patent: Jul. 21, 2015

(54) AUTOMATIC FITTING FOR A VISUAL PROSTHESIS

(71) Applicant: Second Sight Medical Products, Inc., San Fernando, CA (US)

(72) Inventors: Robert J Greenberg, Los Angeles, CA (US); Richard Williamson, Santa Monica, CA (US)

(73) Assignee: Second Sight Medical Products, Inc., Sylmar, CA (US)

( * ) Notice: Subject to any disclaimer, the term of this patent is extended or adjusted under 35 U.S.C. 154(b) by 0 days.

(21) Appl. No.: 13/941,088

(22) Filed: Jul. 12, 2013

(65) Prior Publication Data
US 2013/0304156 A1 Nov. 14, 2013

Related U.S. Application Data

(62) Division of application No. 12/350,019, filed on Jan. 7, 2009, now Pat. No. 8,504,162, and a division of application No. 10/864,590, filed on Jun. 8, 2004, now Pat. No. 7,483,751.

(51) Int. Cl.
A61N 1/05 (2006.01)
A61N 1/36 (2006.01)

(52) U.S. Cl.
CPC ........... A61N 1/36046 (2013.01); A61N 1/0543 (2013.01)

(58) Field of Classification Search
CPC . A61N 1/0543; A61N 1/0529; A61N 1/3605; A61N 1/36046
USPC ............... 607/53, 54, 118, 139, 141; 600/383
See application file for complete search history.

(56) References Cited

U.S. PATENT DOCUMENTS

| 4,573,481 | A | 3/1986 | Bullara |
| 4,628,933 | A | 12/1986 | Michelson |
| 4,837,049 | A | 6/1989 | Byers et al. |
| 5,109,844 | A | 5/1992 | de Juan, Jr. et al. |
| 5,215,088 | A | 6/1993 | Normann et al. |
| 5,935,155 | A | 8/1999 | Humayun et al. |
| 6,400,989 | B1 | 6/2002 | Eckmiller |
| 6,458,157 | B1 * | 10/2002 | Suaning ................. 623/6.63 |
| 6,654,634 | B1 * | 11/2003 | Prass ..................... 600/547 |
| 7,020,531 | B1 * | 3/2006 | Colliou et al. ........... 607/133 |
| 2002/0177882 | A1 * | 11/2002 | DiLorenzo ............... 607/45 |
| 2004/0236389 | A1 | 11/2004 | Fink et al. |
| 2006/0135862 | A1 * | 6/2006 | Tootle et al. ............ 600/373 |

FOREIGN PATENT DOCUMENTS

| WO | WO 00/56393 | 9/2000 |
| WO | WO 01/91852 A1 | 12/2001 |
| WO | WO 2006/089155 A2 | 8/2006 |

* cited by examiner

Primary Examiner — Christopher D Koharski
Assistant Examiner — Natasha Patel
(74) Attorney, Agent, or Firm — Scott B. Dunbar; Alessandro Steinfl; Daniel Ueno

(57) ABSTRACT

The invention is a method of automatically adjusting an electrode array to the neural characteristics of an individual patient. By recording neural response to a predetermined input stimulus, one can alter that input stimulus to the needs of an individual patient. A minimum input stimulus is applied to a patient, followed by recording neural response in the vicinity of the input stimulus. By alternating stimulation and recording at gradually increasing levels, one can determine the minimum input that creates a neural response, thereby identifying the threshold stimulation level. One can further determine a maximum level by increasing stimulus until a predetermined maximum neural response is obtained.

18 Claims, 6 Drawing Sheets

AUTOMATIC FITTING FOR A VISUAL PROSTHESIS

CROSS-REFERENCE TO RELATED APPLICATION(S)

This patent application is a divisional application of U.S. patent application Ser. No. 12/350,019, filed Jan. 7, 2009 for Automatic Fitting for a Visual Prosthesis which is a divisional application of U.S. patent application Ser. No. 10/864,590, filed Jun. 8, 2004, for Automatic Fitting for a Visual Prosthesis, the disclosures of which is incorporated herein by reference.

GOVERNMENT RIGHTS NOTICE

This invention was made with government support under grant No. R24EY12893-01, awarded by the National Institutes of Health. The government has certain rights in the invention.

FIELD OF THE INVENTION

The present invention is generally directed to neural stimulation and more specifically to an improved method of adjusting neural stimulation levels for artificial vision.

BACKGROUND OF THE INVENTION

In 1755 LeRoy passed the discharge of a Leyden jar through the orbit of a man who was blind from cataract and the patient saw "flames passing rapidly downwards." Ever since, there has been a fascination with electrically elicited visual perception. The general concept of electrical stimulation of retinal cells to produce these flashes of light or phosphenes has been known for quite some time. Based on these general principles, some early attempts at devising a prosthesis for aiding the visually impaired have included attaching electrodes to the head or eyelids of patients. While some of these early attempts met with some limited success, these early prosthetic devices were large, bulky and could not produce adequate simulated vision to truly aid the visually impaired.

In the early 1930's, Foerster investigated the effect of electrically stimulating the exposed occipital pole of one cerebral hemisphere. He found that, when a point at the extreme occipital pole was stimulated, the patient perceived a small spot of light directly in front and motionless (a phosphene). Subsequently, Brindley and Lewin (1968) thoroughly studied electrical stimulation of the human occipital (visual) cortex. By varying the stimulation parameters, these investigators described in detail the location of the phosphenes produced relative to the specific region of the occipital cortex stimulated. These experiments demonstrated: (1) the consistent shape and position of phosphenes; (2) that increased stimulation pulse duration made phosphenes brighter; and (3) that there was no detectable interaction between neighboring electrodes which were as close as 2.4 mm apart.

As intraocular surgical techniques have advanced, it has become possible to apply stimulation on small groups and even on individual retinal cells to generate focused phosphenes through devices implanted within the eye itself. This has sparked renewed interest in developing methods and apparatuses to aid the visually impaired. Specifically, great effort has been expended in the area of intraocular retinal prosthesis devices in an effort to restore vision in cases where blindness is caused by photoreceptor degenerative retinal diseases such as retinitis pigmentosa and age related macular degeneration which affect millions of people worldwide.

Neural tissue can be artificially stimulated and activated by prosthetic devices that pass pulses of electrical current through electrodes on such a device. The passage of current causes changes in electrical potentials across visual neuronal membranes, which can initiate visual neuron action potentials, which are the means of information transfer in the nervous system.

Based on this mechanism, it is possible to input information into the nervous system by coding the information as a sequence of electrical pulses which are relayed to the nervous system via the prosthetic device. In this way, it is possible to provide artificial sensations including vision.

One typical application of neural tissue stimulation is in the rehabilitation of the blind. Some forms of blindness involve selective loss of the light sensitive transducers of the retina. Other retinal neurons remain viable, however, and may be activated in the manner described above by placement of a prosthetic electrode device on the inner (toward the vitreous) retinal surface (epiretial). This placement must be mechanically stable, minimize the distance between the device electrodes and the visual neurons, and avoid undue compression of the visual neurons.

In 1986, Bullara (U.S. Pat. No. 4,573,481) patented an electrode assembly for surgical implantation on a nerve. The matrix was silicone with embedded iridium electrodes. The assembly fit around a nerve to stimulate it.

Dawson and Radtke stimulated cat's retina by direct electrical stimulation of the retinal ganglion cell layer. These experimenters placed nine and then fourteen electrodes upon the inner retinal layer (i.e., primarily the ganglion cell layer) of two cats. Their experiments suggested that electrical stimulation of the retina with 30 to 100 uA current resulted in visual cortical responses. These experiments were carried out with needle-shaped electrodes that penetrated the surface of the retina (see also U.S. Pat. No. 4,628,933 to Michelson).

The Michelson '933 apparatus includes an array of photosensitive devices on its surface that are connected to a plurality of electrodes positioned on the opposite surface of the device to stimulate the retina. These electrodes are disposed to form an array similar to a "bed of nails" having conductors which impinge directly on the retina to stimulate the retinal cells. U.S. Pat. No. 4,837,049 to Byers describes spike electrodes for neural stimulation. Each spike electrode pierces neural tissue for better electrical contact. U.S. Pat. No. 5,215,088 to Norman describes an array of spike electrodes for cortical stimulation. Each spike pierces cortical tissue for better electrical contact.

The art of implanting an intraocular prosthetic device to electrically stimulate the retina was advanced with the introduction of retinal tacks in retinal surgery. De Juan, et al. at Duke University Eye Center inserted retinal tacks into retinas in an effort to reattach retinas that had detached from the underlying choroid, which is the source of blood supply for the outer retina and thus the photoreceptors. See, e.g., E. de Juan, et al., 99 Am. J. Ophthalmol. 272 (1985). These retinal tacks have proved to be biocompatible and remain embedded in the retina, and choroid/sclera, effectively pinning the retina against the choroid and the posterior aspects of the globe. Retinal tacks are one way to attach a retinal array to the retina. U.S. Pat. No. 5,109,844 to de Juan describes a flat electrode array placed against the retina for visual stimulation. U.S. Pat. No. 5,935,155 to Humayun describes a retinal prosthesis for use with the flat retinal array described in de Juan.

In addition to the electrode arrays described above, there are several methods of mapping a high resolution camera image to a lower resolution electrode array. U.S. Pat. No. 6,400,989 to Eckmiller describes spatio-temporal filters for controlling patterns of stimulation in an array of electrodes. The assignee of the present applications has three related U.S. patent application Ser. No. 09/515,373, filed Feb. 29, 2000, entitled Retinal Color Prosthesis for Color Sight Restoration; and Ser. No. 09/851,268, filed May 7, 2001, entitled Method, Apparatus and System for Improved Electronic Acuity and Perceived Resolution Using Eye Jitter Like Motion. All three applications are incorporated herein by reference.

Each person's response to neural stimulation differs. In the case of retinal stimulation, a person's response varies from one region of the retina to another. In general, the retina is more sensitive closer to the fovea. Any stimulation, less than the threshold of perception, is ineffective. Stimulation beyond a maximum level will be painful and possibly dangerous to the patient. It is therefore, important to map any video image to a range between the minimum and maximum for each individual electrode. With a simple retinal prosthesis, it is possible to adjust the stimulation manually by stimulating and questioning the patient. As resolution increases, it is tedious or impossible to adjust each electrode by stimulating and eliciting a patient response.

A manual method of fitting or adjusting the stimulation levels of an auditory prosthesis is described in U.S. Pat. No. 4,577,642, Hochmair et al. Hochmair adjusts the auditory prosthesis by having a user compare a received signal with a visual representation of that signal.

A more automated system of adjusting an auditory prosthesis using middle ear reflex and evoked potentials is described in U.S. Pat. No. 6,157,861, Faltys et al. An alternate method of adjusting an auditory prosthesis using the stapedius muscle is described in U.S. Pat. No. 6,205,360, Carter et al. A third alternative using myogenic evoked response is disclosed in U.S. Pat. No. 6,415,185, Maltan.

U.S. Pat. No. 6,208,894, Schulman describes a network of neural stimulators and recorders implanted throughout the body communicating wirelessly with a central control unit. U.S. Pat. No. 6,522,928, Whitehurst, describes an improvement on the system described in Schulman using function electro stimulation also know as adaptive delta modulation to communicate between the implanted devices and the central control unit.

The greatest dynamic range is achieved by setting the minimum stimulation at the threshold of perception and the maximum stimulation level approaching the pain threshold. It is unpleasant for a patient to first concentrate to detect the minimum perception and then be subjected to stimulation near the threshold of pain.

The human retina includes about four million individual photoreceptors. An effective visual prosthesis may include thousands of electrodes. An automated system is needed to adjust individual electrodes in a visual prosthesis for maximum benefit without the need for patient interaction in a long and difficult process.

SUMMARY OF THE INVENTION

The invention is a method of automatically adjusting a retinal electrode array to the neural characteristics of an individual patient. By recording neural response to a predetermined input stimulus, one can alter that input stimulus to the needs of an individual patient. A minimum input stimulus is applied to a patient, followed by recording neural response in the vicinity of the input stimulus. By alternating stimulation and recording at gradually increasing levels, one can determine the minimum input that creates a neural response, thereby identifying the threshold stimulation level. One can further determine a maximum level by increasing stimulus until a predetermined maximum neural response is obtained.

The novel features of the invention are set forth with particularity in the appended claims. The invention will be best understood from the following description when read in conjunction with the accompanying drawings.

DETAILED DESCRIPTION OF THE PREFERRED EMBODIMENTS

The following description is of the best mode presently contemplated for carrying out the invention. This description is not to be taken in a limiting sense, but is made merely for the purpose of describing the general principles of the invention. The scope of the invention should be determined with reference to the claims.

Figure 1:
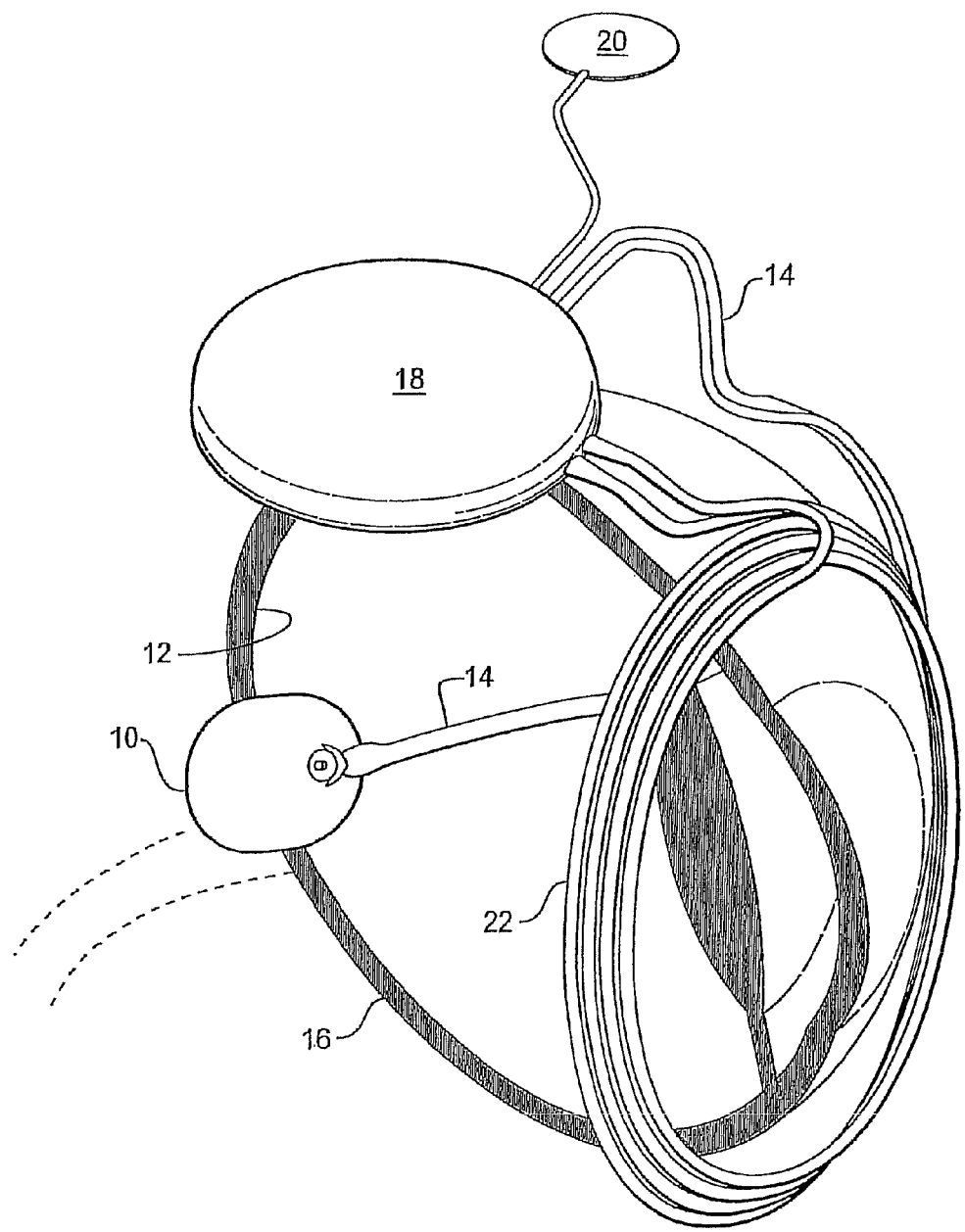
FIG. 1 depicts the preferred retinal prosthesis for implementing the present invention.

FIG. 1 shows the preferred retinal prosthesis. A stimulating electrode array 10 is placed against the outer surface of a retina 12 (epiretinally). A cable 14 pierces a sclera 16 and attaches to an electronic control unit 18. The electronic control unit is attached to the sclera and moves with the sclera. A return electrode 20 may be placed outside the sclera and distant from the retina 12. Alternatively, electrodes in the electrode array 10 may be used a return electrodes. Electricity travels through the body between the stimulating electrode array 10 and return electrode 20, to complete an electrical circuit. The stimulating electrode array 10 is a plurality of tiny electrodes. Each electrode on the stimulating electrode array 10 is as small as possible to maximize the effect of electrical current on the retina, and to fit the maximum number of electrodes on the retina. The return electrode 20, if used, may be quite large by comparison. A coil 22 surrounds the sclera just inside the conjunctiva and acts as an antenna to send and receive data from an external unit (not shown). A matching coil is mounted in a pair of glasses along with a camera for collecting a video image. Power to operate the control unit may also be provided through the coil 22.

The electronics described herein may be in the electronics control unit 18 or mounted externally and communicate through the coil 22. An external solution may initially be simpler and less expensive. With improvements in integrated circuits, it will be cost effective to include all of the control functions described herein within the control unit 18. An entirely implanted solution would greatly reduce the time required to complete the fitting process.

Figure 2:
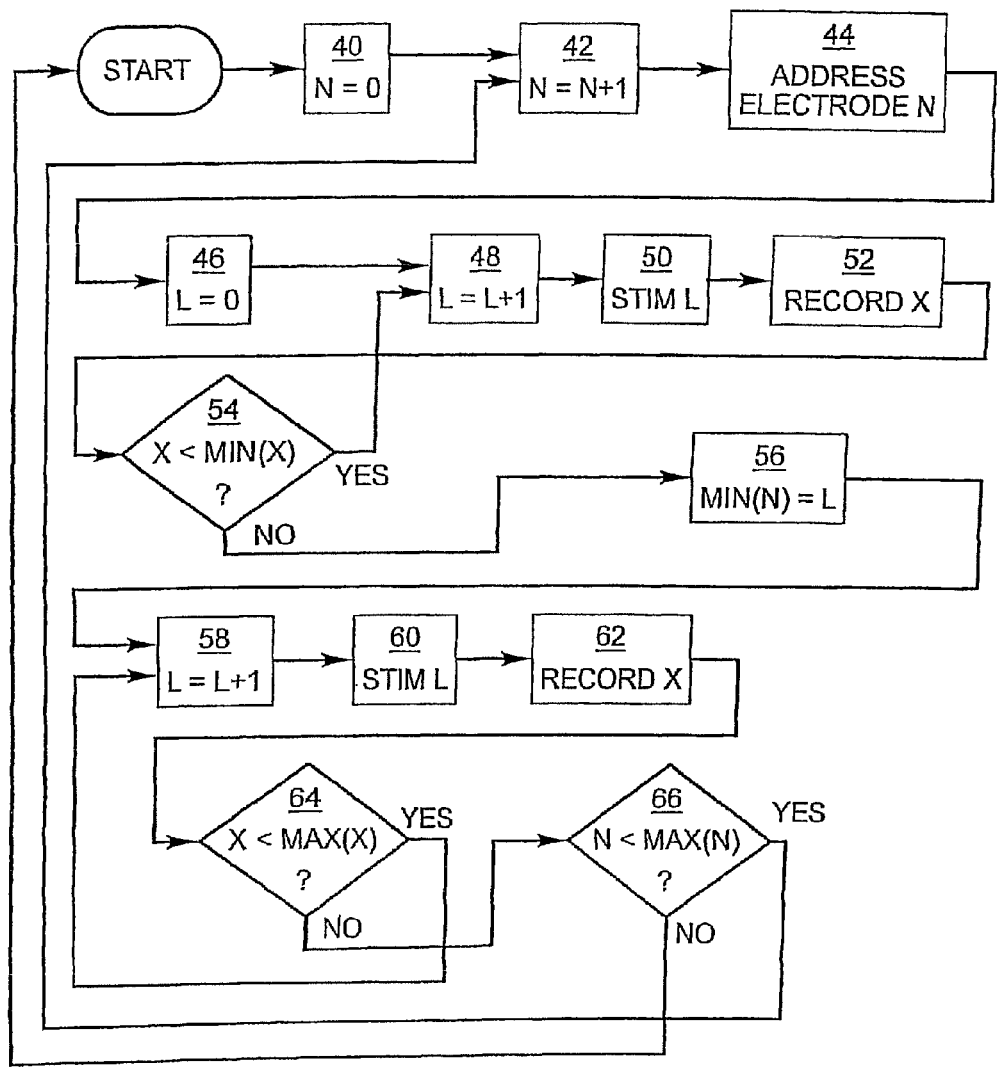
FIG. 2 is a flow chart showing the process of auto fitting an electrode array.

FIG. 2 is a flow chart of the automatic fitting sequence. In the flow chart, the value N is the current (or selected) electrode, X is the neural activity recorded, and L is the level of stimulation. First N is set to 0 40 and them incremented 42. The first electrode, electrode N, is addressed 44. The stimulation level is set to zero 46, and then incremented 48. The neural tissue is stimulated at the minimum level 50. The stimulation is immediately followed by a recording of activity in the neural tissue 52. Alternatively, recording can be done simultaneously by an adjacent electrode. If recording is done simultaneously, one must be careful to distinguish between neural activity and electrical charge from the stimulating electrode. The neural response follows stimulation (see FIG. 4). Simultaneous stimulation and recording requires that the recording phase be longer than the stimulation phase. If so, the stimulation and neural response can be separated digitally. If the recorded neural activity is less than a predetermined level 54, the stimulation level is increased and steps 48-54 are repeated.

In most cases, the preset minimum level is any measurable neural activity. However, perception by the patient is the determining factor. If neural activity is detected and the patient reports no perception, the minimum level must be set higher. Once minimum neural activity is recorded, the stimulation level is saved in memory 56. The level is then further increased 58 and stimulation is repeated 60. Again stimulation is immediately followed by recording neural activity 62. If a predetermined maximum level has not been reached, steps 58-64 are repeated until the predetermined maximum stimulation level is obtained. Once the predetermined maximum stimulation level is obtained, steps 42-64 are repeated for the next electrode. The process is continued until a minimum and maximum stimulation level is determined for each electrode 66.

The maximum stimulation level borders on discomfort for the patient. Because the automatic fitting process is automated, high levels of stimulation are only applied for a few microseconds. This significantly decreases the level of discomfort for the patient compared with stimulating long enough to elicit a response from the patient.

The fitting process is described above as an incremental process. The fitting process may be expedited by more efficient patterns. For example changes may be made in large steps if it the detected response is significantly below the desired response, followed by increasingly small steps as the desired response draws near. The system can jump above and below the desired response dividing the change by half with each step.

Often, neural response in a retina is based, in part, geographically. That is, neurons closer to the fovea require less stimulation than neurons farther from the fovea. Hence once a stimulation is level is set for an electrode, one can presume that the level will be similar for an adjacent electrode. The fitting process may be expedited by starting at a level near the level set for a previously fit adjacent electrode.

Automating the fitting process has many advantages. It greatly expedites the process reducing the efforts of the patient and clinician. Further, the automated process is objective. Patient responses are subjective and may change over time due to fatigue. In some cases, a patent may not be able to provide the required responses due to age, disposition, and/or limited metal ability.

Figure 3:
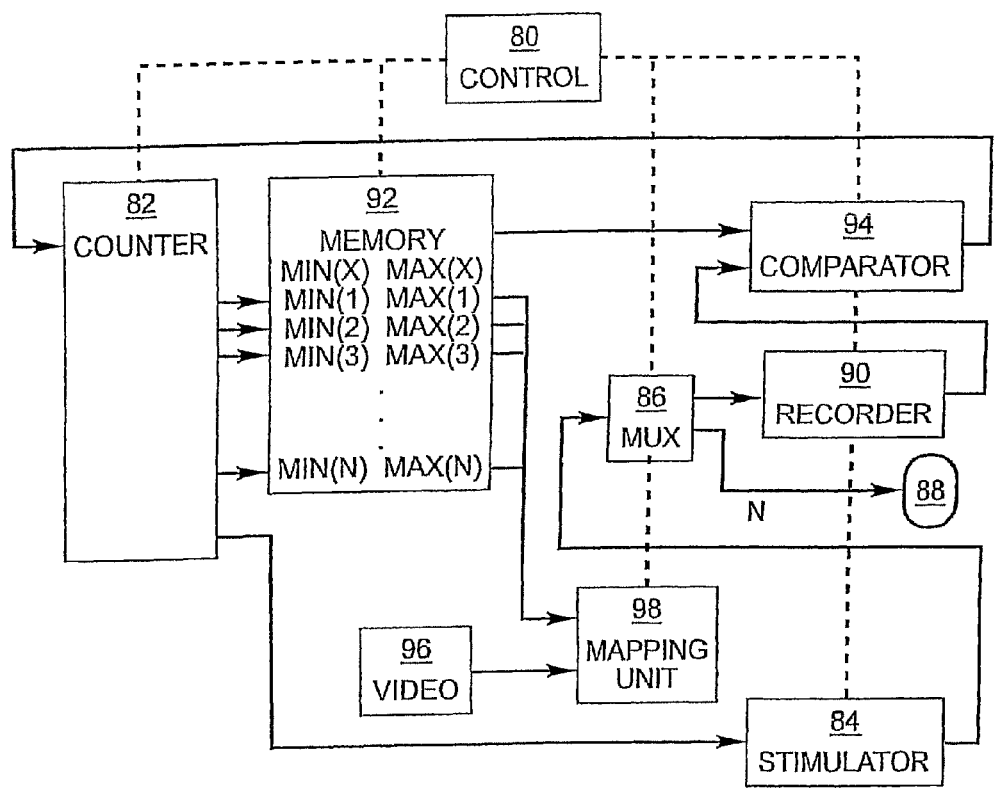
FIG. 3 depicts a block diagram of the retinal prosthesis electronic control unit.

FIG. 3 depicts a block diagram of the control unit. The block diagram is a functional diagram. Many of the functional units would be implemented in a microprocessor. A control unit 80 sets and increments a counter 82 to control the stimulation level of the stimulator 84. The stimulation signal is multiplexed in MUX 86 to address individual electrodes 88. After each stimulation, the addressed electrode returns a neural activity signal to a recorder 90. The signal is compared to the stored minimum or maximum level (stored in a memory 92) in a comparator 94. After programming, a signal from a video source 96, or other neural stimulation source, is adjusted in a mapping unit 98, in accordance with the minimum and maximum levels stored in the memory 92. The adjusted signal is sent to the stimulator 84, which in synchronization with MUX 86 applies the signal to the electrodes 88. The electronics for the control unit could be external or within the implanted prosthesis.

Figure 4:
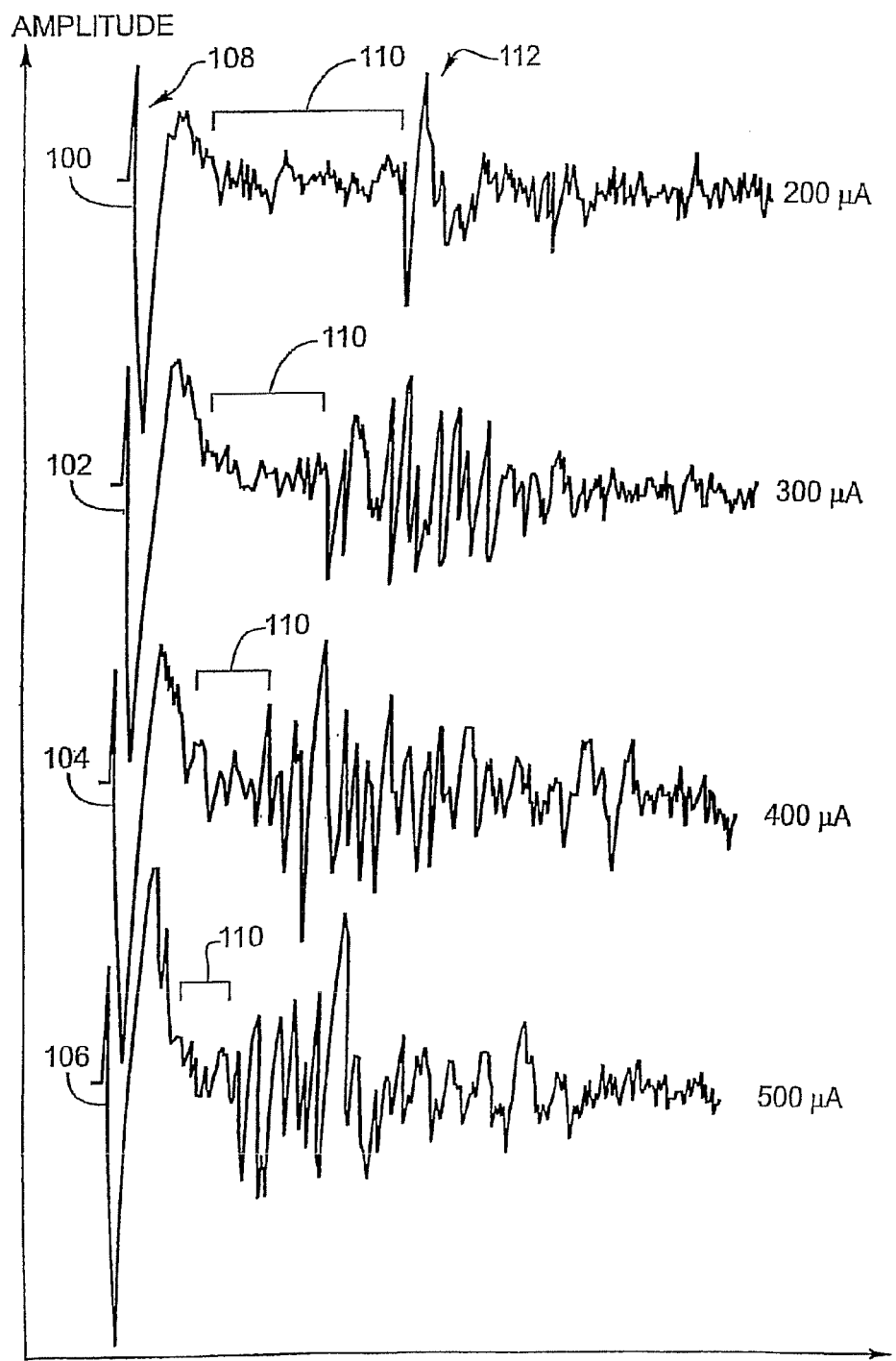
FIG. 4 is a graph depicting a typical neural response to electrical input.

FIG. 4 is a graphical representation of the neural response to electrical stimulus. This figure is derived from actual recordings of a frog retina. Response in a human retina will be similar. The vertical axis is current while the horizontal axis is time. Four curves 100-106 show the response at varying input current levels. An input pulse 108, is followed by a brief delay 110, and a neural response 112. Hence, it is important to properly time the detecting function. Either the stimulating electrode must be switched to a detecting electrode during the brief delay or detecting must occur on another electrode and continue long enough to record the neural response. It should also be noted that the delay period 110 becomes shorter with increased stimulation current. Hence, the system must switch faster from stimulation mode to detecting mode with increased current. The change in delay time may also be used as an additional indication of neural response. That is, the minimum and maximum may be determined by matching predetermined delay times rather than predetermined output levels. As stimulation increases, it becomes more useful to employ an alternate recording means as described in the following alternate embodiments.

In a first alternate embodiment, the recording electrode may be cortical electrode mounted on or near the visual cortex. Temporary external electrodes placed on the scalp proximate to the visual cortex may record neural activity in the visual cortex. This allows the system to account for any variations in neural processing between the retina and the visual cortex. It, however, requires electrodes either implanted in the visual cortex or placed temporarily near the visual cortex. This alternate embodiment may be combined with the preferred embodiment by first using cortical electrodes to perform an initial fitting of the prosthesis in a clinic. Thereafter, retinal recording may be used to readjust the prosthesis for any changes over time.

Figure 5:
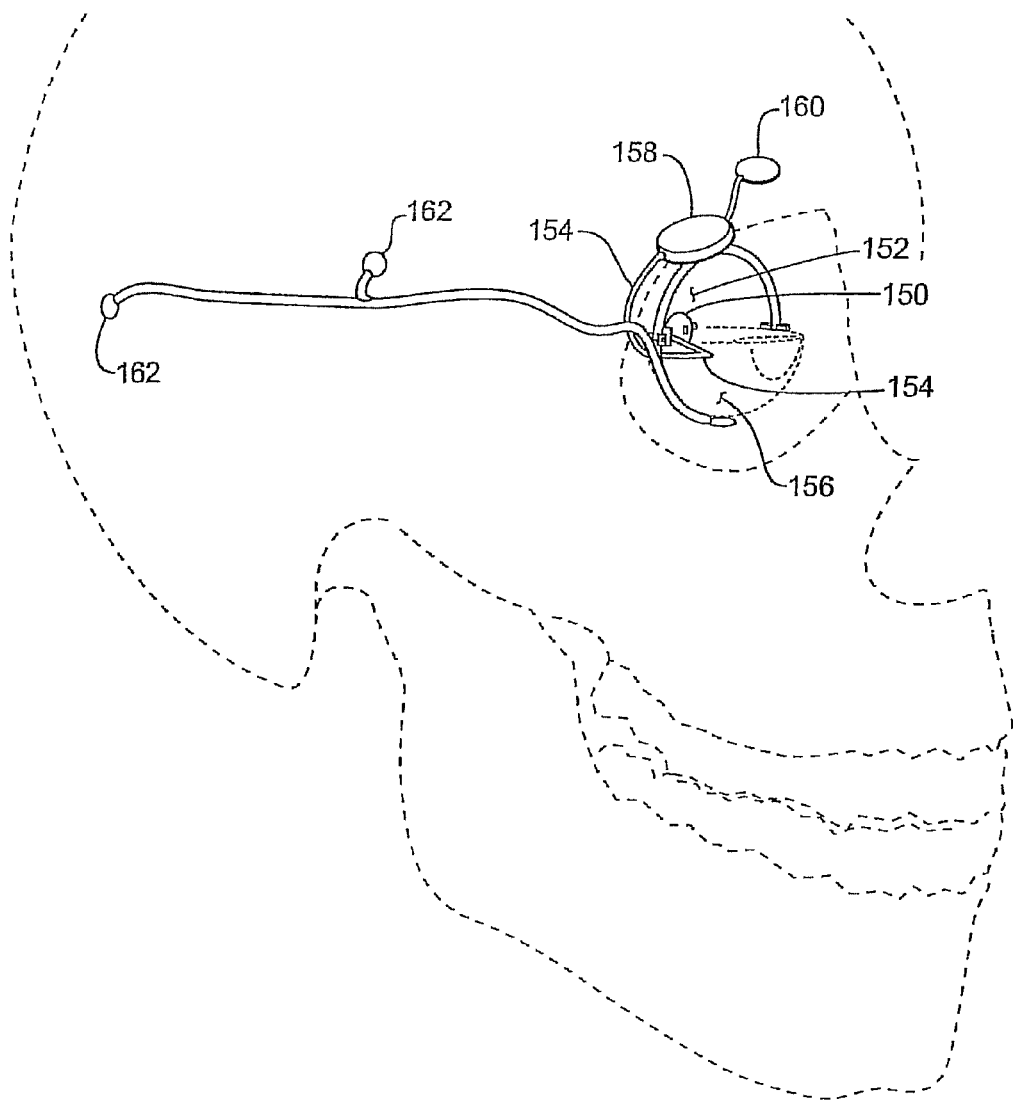
FIG. 5 depicts an alternate retinal prosthesis using cortical recording.

FIG. 5 shows the first alternate retinal prosthesis. A stimulating electrode array 150 is placed against the outer surface of a retina 152 (epiretinally). A cable 154 pierces a sclera 156 and attaches to an electronic control unit 158. A return electrode 160 may be placed distant from the retina 152. The stimulating electrode array 150 is a plurality of tiny electrodes. One or more recording electrodes 162 are placed in near the visual cortex. The recording electrodes may temporary external electrodes, implanted electrodes under the scalp, or electrode implanted within the visual cortex.

In a second alternate embodiment, the recording electrode may be either implanted in the iris, or placed externally near the iris. The iris responds to light, or the perception of light. In response to an increase in electrical stimulation the iris will contract because the body perceives an increase in light entering the eye. Conversely, the iris expands in response to a decrease in electrical stimulation. While the response of the iris is relatively slow, the neurological signals initiating a change in the iris respond quickly. Measuring these signals may provide alternate feed back as to the body's response to the electrical stimulus. Alternatively, an optical device aimed at the eye may detect the movement of the iris.

Figure 6:
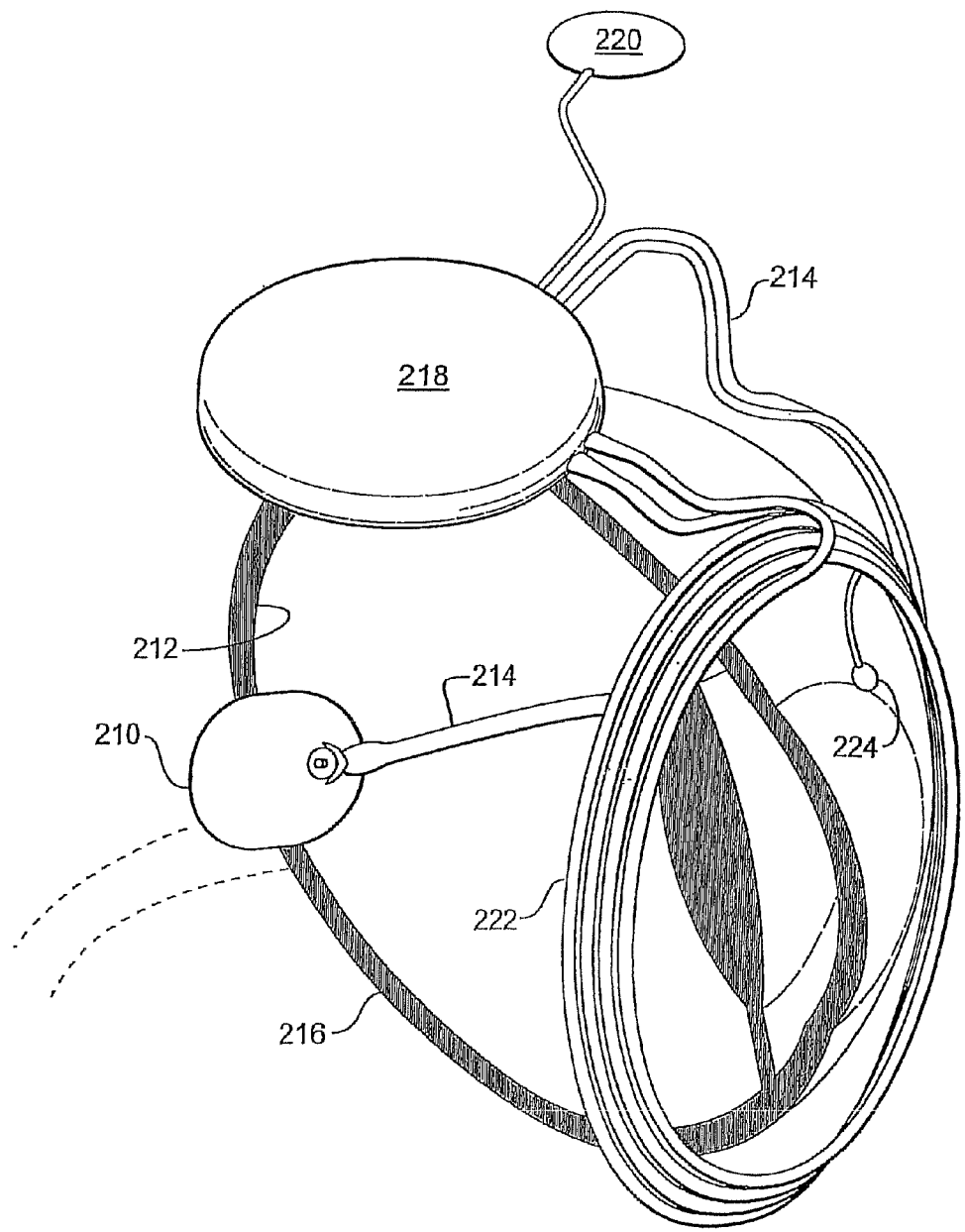
FIG. 6 depicts an alternate retinal prosthesis using iris recording.

FIG. 6 shows the second alternate retinal prosthesis. A stimulating electrode array 210 is placed against the outer surface of a retina 212 (epiretinally). A cable 214 pierces a sclera 216 and attaches to an electronic control unit 218. A return electrode 220 may be placed distant from the retina 212. The stimulating electrode array 210 is a plurality of tiny electrodes. A recording electrode 224 is place in the periphery of the iris sensing electrical stimulus to the iris.

In a third alternate device, electroluminescent pigments may be applied to the retina. Electroluminescent pigments cause an individual cell to glow when it fires it neuro-electrical charge. A camera of the type used for retinal photos may detect neural response by detecting the electroluminescent glow of the applied pigment.

Accordingly, what has been shown is an improved method of stimulating neural tissue for increased resolution. While the invention has been described by means of specific embodiments and applications thereof, it is understood that numerous modifications and variations could be made thereto by those skilled in the art without departing from the spirit and scope of the invention. It is therefore to be understood that within the scope of the claims, the invention may be practiced otherwise than as specifically described herein.

The invention claimed is:

1. A neural stimulation device comprising:
   a neural stimulation driver;
   a stimulating electrode electrically connected to the neural stimulation driver emitting a stimulation signal;
   a neural recorder creating recordings;
   a recording electrode separate from the stimulating electrode and electrically connected to the neural recorder;
   a digital separator separating the recordings to remove the stimulation signal and producing separated recordings;
   a fitting circuit automatically adjusting the neural stimulation driver based on the separated recordings from the neural recorder.

2. The neural stimulation device according to claim 1, wherein the recording electrode is adapted to be located adjacent the stimulating electrode.

3. The neural stimulation device according to claim 1, wherein the recording electrode is adapted to be located in a cortex.

4. The neural stimulation device according to claim 1, wherein the recording electrode is adapted to be located on a scalp.

5. The neural stimulation device according to claim 1, wherein the neural recorder is adapted to record simultaneous with activation of the neural stimulation driver.

6. The neural stimulation device according to claim 1, wherein the neural recorder is adapted to record after activation of the neural stimulation driver.

7. The neural stimulation device according to claim 1, wherein the fitting circuit includes memory for storing stimulation and recording levels.

8. The neural stimulation device according to claim 1, wherein the stimulation and recording levels include threshold and maximum levels.

9. A visual prosthesis comprising:
   a neural stimulation driver;
   a stimulating electrode electrically connected to the neural stimulation driver emitting a stimulation signal;
   a neural recorder creating recordings;
   a recording electrode separate from the stimulating electrode and electrically connected to the neural recorder;
   a digital separator separating the recordings to remove the stimulation signal and producing separated recordings;
   a fitting circuit automatically adjusting the neural stimulation driver based on the separated recordings from the neural recorder.

10. The visual prosthesis according to claim 9, wherein the recording electrode is adapted to be located adjacent the stimulating electrode on an epiretinal surface.

11. The visual prosthesis according to claim 9, wherein the recording electrode is adapted to be located in a visual cortex.

12. The visual prosthesis according to claim 9, wherein the recording electrode is adapted to be located on a scalp near the visual cortex.

13. The visual prosthesis according to claim 9, wherein the recording electrode is adapted to be located in an iris.

14. The visual prosthesis according to claim 9, wherein the recording electrode is adapted to be located external to a body near an iris.

15. The visual prosthesis according to claim 9, wherein the neural recorder is adapted to record simultaneous with activation of the neural stimulation driver.

16. The visual prosthesis according to claim 9, wherein the neural recorder is adapted to record after activation of the neural stimulation driver.

17. The visual prosthesis according to claim 9, wherein the fitting circuit includes memory for storing stimulation and recording levels.

18. The visual prosthesis according to claim 9, wherein the stimulation and recording levels include threshold and maximum levels.

* * * * *